(12) United States Patent
Cheng et al.

(10) Patent No.: US 7,091,336 B2
(45) Date of Patent: Aug. 15, 2006

(54) LYOPHILIZED POWDER OF LENTINAN AND THE PROCESS OF PREPARATION THEREOF

(75) Inventors: Pei Yuan Cheng, Jiangsu (CN); Jing Weng, Jiangsu (CN); Yi Gong Fang, Jiangsu (CN); Guang Cheng, Jiangsu (CN)

(73) Assignee: Nanjing Zhenzhong Bioengineering Co., Ltd., Jiangsu (CN)

( * ) Notice: Subject to any disclaimer, the term of this patent is extended or adjusted under 35 U.S.C. 154(b) by 46 days.

(21) Appl. No.: 10/333,052

(22) PCT Filed: Feb. 28, 2001

(86) PCT No.: PCT/CN01/00311

§ 371 (c)(1),
(2), (4) Date: Jun. 9, 2003

(87) PCT Pub. No.: WO02/07708

PCT Pub. Date: Jan. 31, 2002

(65) Prior Publication Data

US 2004/0242534 A1     Dec. 2, 2004

(30) Foreign Application Priority Data

Jul. 19, 2000     (CN) ................................ 00 1 12407

(51) Int. Cl.
  C07H 1/00     (2006.01)
  A61K 31/335   (2006.01)
(52) U.S. Cl. .................... 536/123.1; 549/200; 514/449

(58) Field of Classification Search ............. 536/123.1, 536/123.12; 549/200; 514/449
See application file for complete search history.

(56) References Cited

U.S. PATENT DOCUMENTS 5,130,127 A * 7/1992 Herlyn .................... 424/155.1
5,648,385 A * 7/1997 Starrett et al. ............. 514/513

FOREIGN PATENT DOCUMENTS

CN     1076112 A    9/1993
CN     1087610 C    7/2002

OTHER PUBLICATIONS

Seljelid, J., Scand. J. Immunol. 1989, 29: 181-92.*
Lee et al., Progress in Plant Polymeric Carbohydrate Research, 7th, berlin, Jul. 1-3, 1992 (12995) 77-80.*
Lee et al. Progress in Plant Polymeric Carbohydrate Research, 7th, Berlin, Jul. 1-3, 1992 (1995) 77-80.*

* cited by examiner

Primary Examiner—James O. Wilson
Assistant Examiner—Paul V. Ward
(74) Attorney, Agent, or Firm—Michael Bednarek; Pillsbury Winthrop Shaw Pittman LLP

(57) ABSTRACT

The present invention discloses an antineoplastic sterile lyophilized powder of lentinan and the process of preparation thereof. The lyophilized powder of lentinan is essentially consisted of 0.50–1.40 parts of lentinan and 50–140 parts of excipient for lyophilization, based on weight. It has good stability. It has improved safety as it does not contain dextran which may cause allergic side effect.

7 Claims, 1 Drawing Sheet

LYOPHILIZED POWDER OF LENTINAN AND THE PROCESS OF PREPARATION THEREOF

Figure 1:
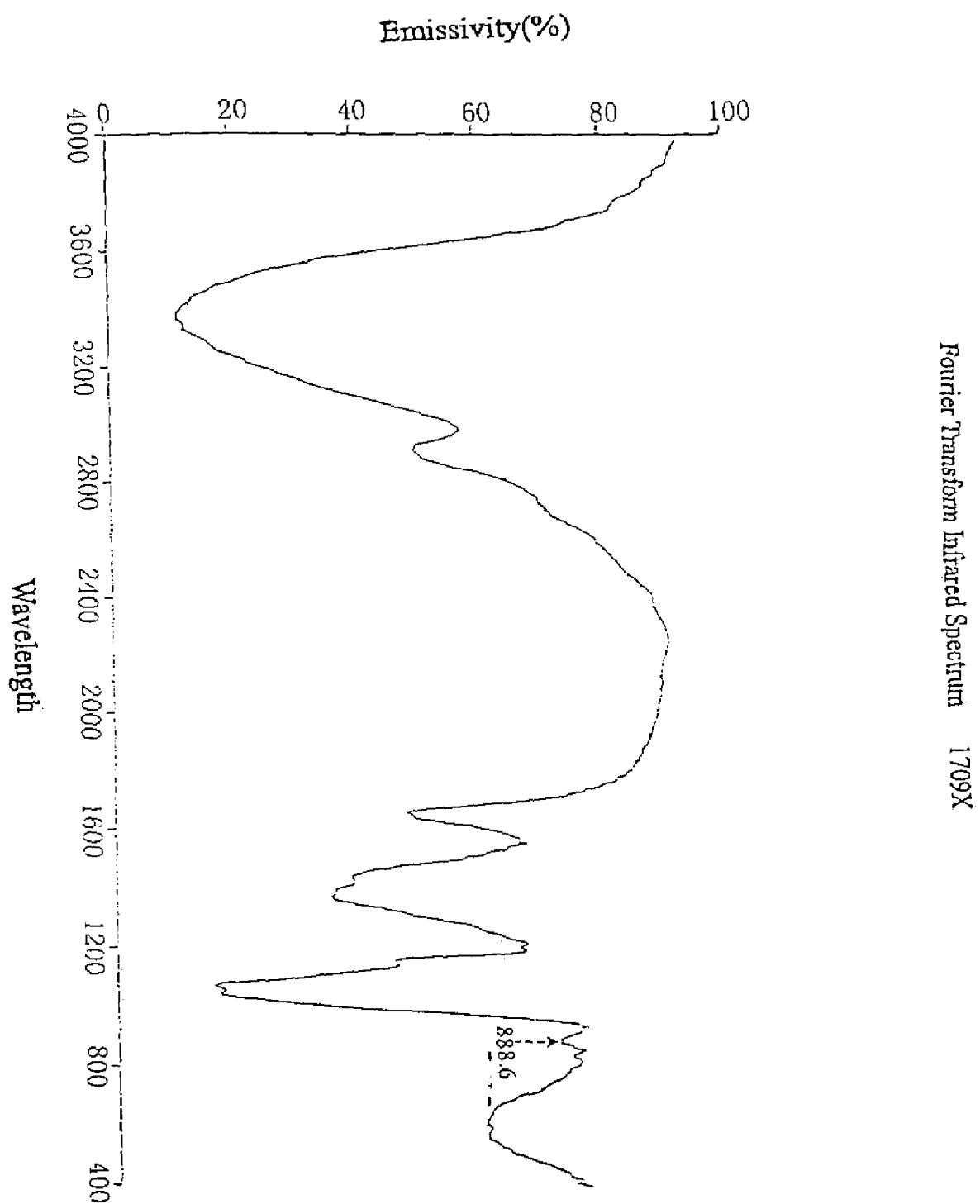

The present invention relates to a biological response modifier (BRM) and the process of preparing thereof, especially, relates to an aseptic antineoplastic lyophilized powder of lentinan for injection and the process of preparation thereof.

Lentinus edodes contains multifold components such as protein, heteropolysaccharide and lentinan etc. Lentinan is a kind of polysaccharides which was extracted, separated and purified from lentinus edodes entity by Japanese scholar Chihara, G. the primary structure of which is glucose with the principal chain of β-(1-3)glucose and side chain of β-(1-6)glucose. According to the report, lentinan is a kind of BRM with strong inhibition to several cancers and prophylactic effect to the chemical carcinogen, virus carcinogen, especially to the micrometastasis after operation. At the same time lentinan has many virtues such as small dosage of administration, little side effect and usage safety. Japanese Health Ministry granted lentinan as a new antineoplastic drug to appear on market in 1985. China has imported the Lyophilized powder of lentinan for injection from Japanese Atinomoto and applied it in clinic since 1988. However the formula of Lyophilized powder of lentinan incorporated from Japan is composed of lentinan, dextran and mannitol. As a kind of product of fermentation, when used in clinic, dextran has been found in several cases that leading to death as its anaphylactic shock.

Chinese Patent Application CN-96116294.5 has disclosed a kind of lentinan injection and the process of preparing thereof. Firstly, dissolve the lentinan in sodium hydroxide solution, then add citrate acid to adjust the pH, and achieve the lentinan injection by filtration and disinfection. It may be effective, but it is different from the present invention in formulation dosage form, molecular weight determination and its distribution of the main product.

It is an object of the present invention to provide a lyophilized powder of lentinan without ingredient that can produce side effect.

It is another object of the present invention to provide a process of preparing lyophilized powder of lentinan without ingredient that can produce side effect.

It is still an object of the present invention to provide a lyophilized powder of lentinan without dextran.

All these and the other objects of the present invention will be illuminated in detail by further description in the following.

Aseptic antineoplastic lyophilized powder of lentinan for injection of the present invention is substantially composed of: 0.50~1.40 parts by weight of lentinan, 50~140 parts by weight of lyophilized excipient.

Furthermore, the aseptic antineoplastic lyophilized powder of lentinan for injection of the present invention is substantially composed of: 0.70~1.40 parts by weight of lentinan, 70~140 parts by weight of lyophilized excipient.

The aseptic antineoplastic lyophilized powder of lentinan for injection of the present invention is also substantially composed of: 0.80~1.20 parts by weight of lentinan, 80~120 parts by weight of lyophilized excipient.

If necessary, the aseptic antineoplastic lyophilized powder of lentinan for injection of the present invention could also be added to other acceptable or mixable additives and therapeutic drugs in medicine. Of course, these additives and therapeutic drugs will not damage the effect of lentinan, and absolutely without dextran.

If necessary, it could also be added to or mixed with other antineoplastic. Preferably, the antineoplastic and auxiliary can be bear bile powder, Redsedum, Ginseng, American ginseng, Chinese cater pillar fungus, *Lucid ganoderma* and *Saussurea involucrate* and so on.

The lyophilized excipient of aseptic antineoplastic lyophilized powder of lentinan for injection of the present invention can be any one of mannitol, glucose, sucrose or lactose, preferably mannitol. If necessary and possible, the mixture of two or three selected from mannitol, glucose, sucrose or lactose also can be used.

The process of preparing aseptic antineoplastic lyophilized powder of lentinan for injection of the present invention can include the following steps: 0.50~1.40 parts by weight of lentinan was taken and dissolved completely in the 20~70 parts by weight of alkali solution, the concentration of alkali solution is 0.5~1.0 mol/L, and then acid solution was added to neutralize the pH of the solution to 6.0~8.0, then mixed with 50~140 parts by weight of lyophilized excipient again, filtered to eliminate the bacteria, subpackaged into ampoule or glass bottle, sealed after lyophilized.

Furthermore, the process of preparing the aseptic antineoplastic lyophilized powder of lentinan for injection of the present invention can also include the following steps: 0.70~1.40 parts by weight of lentinan was taken and dissolved completely in the 20~60 parts by weight of alkali solution, the concentration of alkali solution is 0.5~1.0 mol/L, and then acid solution was added to neutralize the pH of the solution to 6.0~8.0, then mixed with 70–140 parts by weight of lyophilized excipient again, filtered to eliminate the bacteria, subpackaged into ampoule or glass bottles, sealed after lyophilized.

The process of preparing the aseptic antineoplastic lyophilized powder of lentinan for injection can also include the following steps: 0.80~1.20 parts by weight of lentinan was taken and dissolved completely in the 20~80 parts by weight of alkali solution, the concentration of alkali solution is 0.5~1.0 mol/L, and then acid solution was added to neutralize the pH of the solution to 6.0~8.0, then mixed with 40~120 parts by weight of lyophilized excipient again, filtered to eliminate the bacteria, subpackaged into ampoule or glass bottle, sealed after lyophilized.

In the process of preparing aseptic antineoplastic lyophilized powder of lentinan for injection of the present invention, the applied lyophilized excipient could be one of mannitol, glucose, sucrose or lactose, preferably mannitol. The applied alkali is sodium hydroxide and the applied acid is hydrochloric acid.

In the process of preparing aseptic antineoplastic lyophilized powder of lentinan for injection of the present invention, lentinan is mixed evenly with lyophilized excipi ent, and then filtered to eliminate the bacteria, determining the content (the content determined by the classical anthrone-sulfuric process), filled into the ampoule or glass bottle, lyophilize, sealed or gland bushed, leak checked, paste labeled. The procedures before sealed or gland bushed should be proceeded under asepsis condition.

The applied lentinan of the present invention includes single lentinan and multi-component lentinan, which are well-known in the prior art and can be obtained from market. Furthermore, the extraction, separation, purification of lentinan could be referred to Nature 1965, 222, 687–8 and CN-94115876 and the other patent or non-patent documents. These documents mentioned above are incorporated into the present invention herein.

The lyophilized powder of lentinan for injection of the present invention is used before operation or before chemotherapy, 1~2 mg each time, twice a week; or 2 mg each time, once or twice a week. When applied, the lyophilized powder of lentinan for injection should be dissolved in 250 ml saline or glucose solution, and administered by phleboclysis. When treating the malignant pleural effusion and ascites, the dosage is 4–8 mg each time by intracavitary. Specific case should obey the doctor's prescription.

2. Carbon-nuclear Magnetic Resonance Spectrum (Tab. 1)

TAB. 1

| C | Sample of Lentinan | Lentinan[6] | Analysis |
|---|---|---|---|
| 1 | 104.6 | 104.6 | B-D- (1–3) glucose |
| 2 | 74.5 | 74.3 | B-D- (1–3) glucose |
| 3 | 87.7 | 87.7 | B-D- (1–3) glucose |
| 4 | 70.2 | 70.2 | B-D- (1–3) glucose |
| 5 | 77.8 | 77.9 | B-D- (1–3) glucose |
| 6 | 62.5 | 62.5 | B-D- (1–3) glucose |
| 1' | 104.9 | 104.6 | B-D- (1–6) glucose |
| 6' | 71.5 | 71.5 | B-D- (1–6) glucose |

3. Figure of Infra-red Spectrum (FIG. 1)

4. Molecular Formula

The result of the trace of element analysis indicates that its molecular formula is $(C_6H_{10}O_5)_n$ 5. Chemical Structural Formula Combined the chemical reaction such as Periodic acid reaction, Smith degradation reaction with optical spectrum analysis, the primary structure of the lentinan displays as the following:

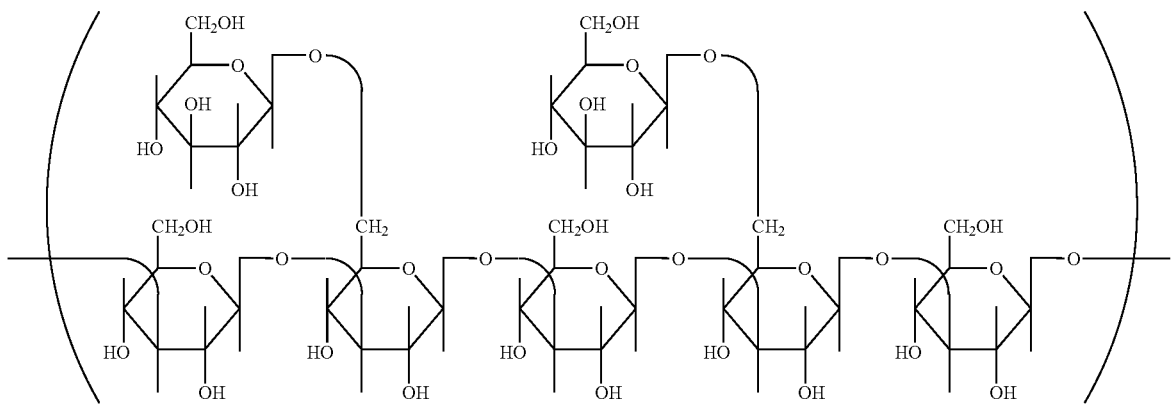

The lyophilized powder of lentinan for injection of the present invention has been tested in clinic and its clinic effect is definite, the stability of preparation is very good and because it does not contain the dextran that could bring the side effect of anaphylaxis, its application in clinic is more safety. Moreover, because it does not containing dextran in the lyophilized powder of lentinan, its content determination need not separation the dextran by special column chromatography equipment and the classical anthrone-sulfuric process can be applied directly, which make the content determination more accurate and simple.

I. The Molecular Weight, Molecular Formula, Chemical Structural Formula of the Product of the Present Invention 1. The Determination of Molecular Weight By high performance gel permeation chromatography and universal correction curve, most of its molecular weight is determined to be between 400,000 and 800,000 Dalton.

II. Result and Conclusion of the Stability of the Preparation

Tested by the influencing factor test such as the high-temperature test (40° C., 60° C., 80° C.), high humidity test (RH92.5%, RH75%, 25° C.) and light irradiation test (4000 Lx), appearance character, clarity after dissolving, pH value, content, impurity and asepsis test of the product of the present invention meet the request.

After three-month speed-up test (40° C. RH 75%), the review result shows that the appearance character, clarify after dissolving, pH value, content, impurity and asepsis test of the product of the present invention meet the request.

The product of the present invention was observed and analyzed respectively in 1, 3, 5, 12, 18 and 24 month at room temperature after being prepared. By way of the periodical check of the samples, all items meet the request. So the effective period is at least two years.

All raw materials and excipient of the present invention could be obtained from market. The applied excipients are solid for injectable grade except pointing out specially.

The following examples will further indicate the present invention. Although the examples are limited in description, it can not limit the extent of the application of the present invention.

In the present invention, all the portions and quantities are the unit of weight based on the gross weight other than mentioned specially.

EXAMPLE 1

The example uses clinical trial phase II and III to prove the excellent effect of the lyophilized powder of lentinan for injection of the present invention.

I. Clinical Trial of the Phase II:

The double-blind process and stochastic process are adopted to proceed the clinical trial of the phase II via the hospital appointed by nation. Combined chemotherapy and placebo (lyophilized powder) being the controlling group and combined chemotherapy and lyophilized powder of lentinan being the testing group, 240 patients with different kinds of cancer are tested. The result illuminates that there are CR+PR 67 examples in the 108 examples of the testing group, and the total effective rate is 62%; CR+PR 44 examples in 104 examples of the controlling group, and the total effective rate is 43.2%. Compared both result, the P<0.01, in which the total effective rate of the gastric cancer in the testing group is 56.6%, the total effective rate of the controlling group is 19.4%, the P<0.01, the total effective rate of the non-small cell lung cancer (NSCLC) in the testing group is 33.3%, the total effective rate of the controlling group is 19.5%, the P<0.01, the total effective rate of the controlling group is 11.5%, the P<0.05. Compared the effect of pre-treatment and post-treatment, the variation rate of lymphocytic cell conversion, NK cytoactive and the rate of $T_4/T_8$ of the testing group are remarkably higher than those of the controlling group, the P<0.01. The effective rate of preliminary using the lentinan to treat the malignant pleural effusion and ascites is 76.5% (13/17), which is similar to that of the foreign literature.

II. The Clinical Trial of the Phase III:

Under the leading of Chinese Medical Association, the Cancer Hospital of Zhongshan Medical University as the responsible hospital, about 40 hospitals in China take part in the clinical trial of the phase III and examines further the clinical effect and the adverse reaction of the lentinan. They complete the 1106 evaluable cases, including 1047 cases with systemic administration and 59 cases with malignant pleural effusion and ascites.

1. The total effective rate of the combined chemotherapy group (565 cases) is 41.1%, Compared with the controlling group (301 cases) which is 25.2%, the effective rate of the two groups are of significant difference (P<0.01), in which the total effective rate of gastric cancer and NSCLC are obviously higher than the controlling group (P<0.01). The same kind of Japanese products company have the chemotherapy enhancement effect of NSCLC hasn't been reported before.
2. malignant pleural effusion and ascites: the total effective rate is 52.5% in 59 cases.
3. At the same time, this test also observes the patients' variation of cellular immune function, and the result shows that the three testing index (NK cytoactive, $T_3$, $T_{4/8}$) are obviously higher than that of the controlling group, and all kinds of main cases display that the lentinan's value enhances the function of cellular immunity.
4. Active State (PS)

There are 1647 cases in the group. The PS of 28.5% patients in the combined chemotherapy group (565 cases) have been improved after treatment (post-treatment compared with pretreatment, there exists significant difference, P<0.01), yet in the controlling group, only 6.8% patient's PS have been improved (compared with pretreatment, there have not significant difference after treatment, P>0.05), compared with the controlling group, the testing group have significant difference (P<0.01).

5. Reducing the Side-effect of Radiotherapy and Chemotherapy

Combined chemotherapy, post-operation combined chemotherapy: The falling incidence rate of $WBC.P_1$ in testing group is significantly lower than that of the controlling group (P<0.01). Gastrointestinal toxicity, liver function lesion in the testing group is also lower than that of the controlling group (P<0.01). The incidence rate of nausea vomitus in testing group is significantly lower than that of the controlling group (P<0.01). It has not been reported in clinic that the like products of Japanese Atinomotocompany have this very effect.

6. Side-effect

Only three cases of side-effect occurred, occupying 0.27% among the 1121 cases that applied lentinan systemically, including two cases of facial flush, one case of chest discomfort, which could restore in short time after slowing the drip speed or withdrawing drug. In 469 cases of the clinical trial of the phase II, III of Japanese product, 32 cases of side-effect occured, occupying 6.8%.

EXAMPLE 2

2.00 g lentinan material for injection (purity 98% was taken, 60 ml 1M sodium hydroxide solution was added. The lentinan was swelt naturally, then stirred to make them dissolve completely. Small amount of water for injection was added to dilute, then stirred equally. 1M hydrochloric acid was added to neutralize the pH of the solution to 6.8–7.0 1000 ml commercial 20% mannitol injection solution was added, and stirred equally, aseptic filtrated, the content (the content determination used the classical anthrone-sulfuric process) was determined. Water for injection was added to achieve the concentration that each 2 ml solution contains 1 mg lentinan, subpackaged into 2 ml/ampoule or bottle, then lyophilized and dried, sealed, leak checked, eye checked, labeled and the end product was achieved at last.

EXAMPLE 3

3 g lentinan for injection was taken, dissolved fractionally in 100 ml 0.8M sodium hydroxide solution when stirred until completely dissolved, and then 0.8M hydrochloric acid was slowly added to neutralize the pH of the solution to 7.0–7.2. Getting 300 g commercial mannitol for injection was taken, and 1600 ml water for injection was added and to dissolve it by heating, then 0.1% W/V activated carton for injection was added and heated for 15 min at 85° C., filtered by using No. 3 sand core filter candle when cooled to 60° C., then the lentinan solution was added into the filtering solution, thereafter proceed asepsis filtration by using the filter membrane, the content was determined, then water for injection was added to achieve the concentration that each 2 ml solution contain 1.5 mg lentinan, the ampoule was filled to 2 ml/ampoule, moved into the freezing room to be lyophilized and dried, then it was taken out and the ampoule or bottle was sealed, leak checked and labeled, and the end product was achieved at last.

EXAMPLE 4

4.00 g lentinan material for injection (purity 98%) (obtained from market) was taken, 120 ml 1M sodium hydroxide solution was added. The lentinan was swelt naturally, then stirred to make them dissolve completely. Small amount of water for injection was added to dilute, then stirred equally. 1M hydrochloric acid was added to neutralize the pH of the solution to 6.8–7.0. 400 g mannitol injection was added, and water for injection was added until the total volume was 3200 ml, stirred equally and aseptic filtrated, the content was determined. Water for injection was added to achieve the concentration that each 2 ml solution contains 2 mg lentinan, subpackaged into 2 ml/ampoule or bottle, then lyophilized and dried, decrated, sealed, leak checked, eye checked and labeled.

EXAMPLE 5

2.00 g lentinan material for injection (purity 98%) was taken, 50 ml 1M sodium hydroxide solution was added. The lentinan was swelt naturally, then stirred to make them dissolve completely. Suitable amount of water for injection was added to dilute, then stirred equally. 1M hydrochloric acid was added to neutralize the pH of the solution to 6.8–7.0. 200 g glucose for injection was added, and 1800 ml water for injection was added, stirred equally and aseptic filtrated, the content was determined. Water for injection was added to achieve the concentration that each 2 ml solution contains 2 mg lentinan, subpackaged into 2 ml/ampoule or bottle, then lyophilized and dried, decrated, sealed, leak checked, eye checked and labeled.

EXAMPLE 6

2.00 g lentinan material for injection (purity 98%) was taken, 60 ml 1M sodium hydroxide solution was added. The lentinan was swelt naturally, then stirred to make them dissolve completely. Suitable amount of water for injection was added to dilute, then stirred equally. 1M hydrochloric acid was added to neutralize the pH of the solution to 6.8–7.0. 200 g lactose for injection was added, and 3200 ml water for injection was added, stirred equally and aseptic filtrated, the content was determined. Water for injection was added to achieve the concentration that each 2 ml solution contains 1 mg lentinan, subpackaged into 2 ml/ampoule or bottle, then lyophilized and dried, decrated, sealed, leak checked, eye checked and labeled.

EXAMPLE 7

6.00 g lentinan material for injection (purity 98%) was taken, 180 ml 1M sodium hydroxide solution was added. The lentinan was swelt naturally, then stirred to make them dissolve completely. Small amount of water for injection was added to dilute, then stirred equally. 1M hydrochloric acid was added to neutralize the pH of the solution to 6.8~7.0. 400 g mannitol for injection was added, and 3200 ml water for injection was added, stirred equally and aseptic filtrated, the content was determined. Water for injection was added to achieve the concentration that each 2 ml solution contains 3 mg lentinan, subpackaged into 2 ml/ampoule or bottle, then lyophilized and dried, decreated, sealed, leak checked, eye checked and labeled.

EXAMPLE 8

6.00 g lentinan material for injection (purity 98%) was taken, 180 ml 1M sodium hydroxide solution was added. The lentinan was swelt naturally, then stirred to make them dissolve completely. Small amount of water for injection was added to dilute, then stirred equally. 1M hydrochloric acid was added to neutralize the pH of the solution to 8.8~7.0. 400 g glucose for injection was added, and 3200 ml water for injection was added, stirred equally and aseptic filtrated, the content was determined. Water for injection was added to achieve the concentration that each 2 ml solution contains 3 mg lentinan, subpackaged into 2 ml/ampoule or bottle, then lyophilized and dried, decrated, sealed, leak checked, eye checked and labeled.

EXAMPLE 9

8.00 g lentinan material for injection (purity 98%) was taken, 240 ml 1M sodium hydroxide solution was added. The lentinan was swelt naturally, then stirred to make them dissolve completely. Small amount of water for injection was added to dilute, then stirred equally. 1M hydrochloric acid was added to neutralize the pH of the solution to 6.8~7.0. 400 g sucrosem for injection was added, and 3200 ml water for injection was added, stirred equally and aseptic filtrated, the content was determined. Water for injection was added to achieve the concentration that each 2 ml solution contains 4 mg lentinan, subpackaged into 2 ml/ampoule or bottle, then lyophilized and dried, decrated, sealed, leak checked, eye checked and labeled.

EXAMPLE 10

8.00 g lentinan material for injection (purity 98%) was taken, 240 ml 1M sodium hydroxide solution was added. The lentinan was swelt naturally, then stirred to make them dissolve completely. Small amount of water for injection was added to dilute, then stirred equally. 1M hydrochloric acid was added to neutralize the pH of the solution to 6.8–7.0. 400 g glucose for injection was added, and 3100 ml water for injection was added, stirred equally and aseptic filtrated, the content was determined. Water for injection was added to achieve the concentration that each 2 ml solution contains 4 mg lentinan, subpackaged into 2 ml/ampoule or bottle, then lyophilized and dried, decrated, sealed, leak checked, eye checked and labeled.

EXAMPLE 11

8.0 lentinan material for injection (purity 98%) was taken, 240 ml 1M sodium hydroxide solution was added. The lentinan was swelt naturally, then stirred to make them dissolve completely. Small amount of water for injection was added to dilute, then stirred again. 1M hydrochloric acid was added to neutralize the pH of the solution to 6.8~7.0. 400 g lactose for injection was added, and 3100 ml water for injection was added, stirred equally and aseptic filtrated, the content was determined. Water for injection was added to achieve the concentration that each 2 ml solution contains 4 mg lentinan, subpackaged into 2 ml/ampoule or bottle, then lyophilized and dried, decorated, sealed, leak checked, eye checked and labeled.

EXAMPLE 12

Besides using lentinan for injection 8.0 g (purity 98%), adding 240 ml 0.8M sodium hydroxide solution, adding hydrochloric acid solution to adjust the pH of the solutions 6.0~6.2, and then adding mannitol for injection 400 mg and adding water for injection 3100 ml, the rest is the same as example 11.

EXAMPLE 13

Besides using lentinan for injection, 4.0 g (purity 98%), adding 200 ml 0.8M sodium hydroxide solution, adding hydrochloric acid solution to adjust the pH of the solution pH to 6.3–6.4, and then adding lactose for injection 200 g, adding water for injection 3100 ml, the rest is the same as example 5.

EXAMPLE 14

Besides using lentinan for injection 4.0 g (purity 98%), adding 50 ml 0.8M sodium hydroxide solution, adding hydrochloric acid solution to adjust the pH of the solution to 6.5–6.6, and then adding sucrose for injection 200 g, adding water for injection 3100 ml, the rest is the same as example 4.

EXAMPLE 15

Besides using lentinan for injection 1.0 g (purity 98%), adding 50 ml 0.8 M sodium hydroxide solution, adding hydrochloric acid solution to adjust the pH of the solution to 6.0–6.2, and then adding mannitol for injection 200 g, adding water for injection 3100 ml, the concentration being 0.5 mg each 2 ml, the rest is the same as example 4.

EXAMPLE 16

Besides using lentinan for injection 1.0 g (purity 98%), adding 50 ml 1M sodium hydroxide solution, adding hydrochloric acid solution to adjust the pH of the solution to 7.0–7.2, and then adding glucose for injection 200 g, adding water for injection 3200 ml, the rest is the same as example 15.

EXAMPLE 17

Besides using lentinan for injection 1.0 g (purity 98%), adding 50 ml 0.8M sodium hydroxide solution, adding hydrochloric acid solution to adjust the pH of the solution to 7.4–7.6, and then adding sucrose for injection 200 g, adding water for injection 3200 ml, the rest is the same as example 15.

EXAMPLE 18

Besides using lentinan for injection 1.0 g (purity 98%), adding 50 ml 0.8M sodium hydroxide solution, adding citric acid solution to adjust the pH of the solution to 7.6–7.8, and then adding lactose for injection 200 g, adding water for injection 3200 ml, the rest is the same as example 15.

EXAMPLE 19

Besides using lentinan for injection 2.0 g (purity 98%), adding 60 ml 0.8M sodium hydroxide solution, adding hydrochloric acid solution to adjust the pH of the solution to 7.8~8.0, and then adding mannitol for injection 200 g, adding water for injection 3100 ml, the rest is the same as example 6.

EXAMPLE 20

Besides using lentinan for injection 2.0 g (purity 98%), adding 50 ml 1.0M sodium hydroxide solution, adding hydrochloric acid solution to adjust the pH of the solution to 7.8–8.0, and then adding glucose for injection 100 g, adding mannitol for injection 100 g, adding water for injection 3100 ml, the rest is the same as example 6.

EXAMPLE 21

Besides using lentinan for injection 2.0 g (purity 98%), adding 100 ml 1.0M sodium hydroxide solution, adding hydrochloride acid solution to adjust the pH of the solution to 7.0~7.1, and then adding lactose for injection 100 g, adding mannitol for injection 100 g, adding water for injection 3000 ml, the rest is the same as example 6.

In the present invention, the examples are only used to illuminate. But they can not limit the extent of the claim of the present invention, any improvement and alternation should be calculated into the extent of the present invention and be limited by the claim of the present invention.

What is claimed is:

1. A process of preparing an aseptic antineoplastic lyophilized powder of lentinan for injection, comprising: lentinan 0/50–1.40 parts by weight taken and dissolved in alkali solution 20–70 parts by weight, the concentration of alkali solution is 0.5–1.0 mol/L, and then acid solution is added to neutralize the pH to 6.0–8.0, thereafter, mixing with 50–140 parts by weight of lyophilized excipient, filtered to eliminate bacteria, subpackaged into an ampoule or bottle, sealed after lyophilization and dried to obtain the final product.

2. A process of preparing an aseptic antineoplastic lyophilized powder of lentinan for injection according to claim 1, comprising: 0.70–1.40 parts by weight of lentinan taken and dissolved in 20–60 parts by weight of alkali solution, the concentration of alkali solution is 0.5–1.0 mol/L, and then acid solution is added to neutralize the pH to 6.0–8.0, thereafter, mixing with 70–140 parts by weight of lyophilized excipient, filtered to eliminate bacteria, subpackaged into an ampoule or bottle, and sealed after lyophilization.

3. A process of preparing an aseptic antineoplastic lyophilized powder of lentinan for injection according to claim 1, comprising: 0.70–1.40 parts by weight of lentinan taken and dissolved in 20–60 parts by weight of alkali solution, the concentration of alkali solution is 0.5–1.0 mol/L, and then acid solution is added to neutralize the pH to 6.0–8.0, thereafter, mixing with 40–120 parts by weight of lyophilized excipient, filtered to eliminate bacteria, subpackaged into an ampoule or bottle, and sealed after lyophilization.

4. The process of preparing an aseptic antineoplastic lyophilized powder of lentinan for injection according to claim 1, wherein said lyophilized excipient is selected from the group consisting of mannitol, glucose, sucrose and lactose.

5. The process of preparing an aseptic antineoplastic lyophilized powder of lentinan for injection according to claim 1, wherein said lyophilized excipient is mannitol.

6. The process of preparing an aseptic antineoplastic lyophilized powder of lentinan for injection according to claim 1, wherein said alkali is sodium hydroxide.

7. The process of preparing an aseptic antineoplastic lyophilized powder of lentinan for injection according to claim 1, wherein said acid is hydrochloric acid.

* * * * *